(12) United States Patent
Stowell et al.

(10) Patent No.: US 9,006,176 B2
(45) Date of Patent: Apr. 14, 2015

(54) CHEMICALLY AND THERMODYNAMICALLY STABLE INSULIN ANALOGUES AND IMPROVED METHODS FOR THEIR PRODUCTION

(71) Applicant: AmideBio LLC, Boulder, CO (US)

(72) Inventors: Michael H. B. Stowell, Boulder, CO (US); Mikhail Plam, Boulder, CO (US)

(73) Assignee: AmideBio LLC, Boulder, CO (US)

( * ) Notice: Subject to any disclaimer, the term of this patent is extended or adjusted under 35 U.S.C. 154(b) by 0 days.

(21) Appl. No.: 13/653,269

(22) Filed: Oct. 16, 2012

(65) Prior Publication Data

US 2013/0096057 A1    Apr. 18, 2013

Related U.S. Application Data

(60) Provisional application No. 61/548,721, filed on Oct. 18, 2011.

(51) Int. Cl.
| | |
|---|---|
| *A61K 38/28* | (2006.01) |
| *A61P 3/10* | (2006.01) |
| *A61P 7/12* | (2006.01) |
| *C07K 14/62* | (2006.01) |

(52) U.S. Cl.
CPC ............ *C07K 14/62* (2013.01); *C07K 2319/00* (2013.01)

(58) Field of Classification Search
CPC .... A61K 38/28; C07K 14/62; C07K 2319/00; A61P 7/12; A61P 3/10
USPC .......................................................... 514/6.2
See application file for complete search history.

(56) References Cited

U.S. PATENT DOCUMENTS

| | | | |
|---|---|---|---|
| 5,962,267 | A | 10/1999 | Shin et al. |
| 8,192,957 | B2 | 6/2012 | Weiss |
| 8,337,817 | B2 | 12/2012 | Nagata et al. |
| 8,501,440 | B2 | 8/2013 | Weiss |
| 2004/0014169 | A1 | 1/2004 | Vogeli et al. |
| 2005/0039235 | A1* | 2/2005 | Moloney et al. ............... 800/288 |
| 2007/0129284 | A1 | 6/2007 | Kjeldsen et al. |
| 2008/0057004 | A1 | 3/2008 | Bell et al. |
| 2008/0146492 | A1* | 6/2008 | Zimmerman et al. ............ 514/3 |
| 2009/0169640 | A1 | 7/2009 | Oki et al. |
| 2010/0009898 | A1 | 1/2010 | Nielsen et al. |
| 2010/0099601 | A1 | 4/2010 | Weiss |
| 2010/0273704 | A1 | 10/2010 | Korsmeyer et al. |
| 2010/0323956 | A1 | 12/2010 | Schellenberger et al. |
| 2011/0059887 | A1 | 3/2011 | Weiss |
| 2011/0077197 | A1* | 3/2011 | Habermann et al. ............ 514/6.4 |
| 2011/0112990 | A1 | 5/2011 | Stowell et al. |
| 2011/0166064 | A1 | 7/2011 | Weiss |
| 2014/0315798 | A1 | 10/2014 | Stowell et al. |

FOREIGN PATENT DOCUMENTS

| | | |
|---|---|---|
| WO | WO 95/16708 A1 | 6/1995 |
| WO | WO2009/087081 A2 * | 7/2009 |

OTHER PUBLICATIONS

Hua et al., "Design of an active ultrastable single-chain insulin analog: synthesis, structure, and therapeutic implications," J. Biol. Chem. 283:14703-716 (2008).*
pTrcHis2 A, B, and C user manual, Invitrogen. Cat. No. V365-50. Revised Aug. 26, 2009.*
Chang et al., "Human insulin production from a novel mini-proinsulin which has high receptor-biding activity," Biochem J. 329:631-635 (1998).*
pTrcHis2 A, B, and C user manual, Invitrogen. Cat. No. V365-50. Revised Ausut 26, 2009.*
Hua, et al. Design of an active ultra stable single-chain insulin analog: synthesis, structure, and therapeutic implications. J. Biol. Chem. 2008; 283(21):14703-14716.
International search report and written opinion dated Feb. 11, 2013 for PCT/US2012/060459.
Invitrogen. pTrcHis2 A, B ad C User Manual. Catalog No. V365-20. Munual Part No. 25-0096. Aug. 26, 2009. Retrieved on Jan. 21, 2013. <url:tools.invitrogen.com/content/sfs/manuals/ptrchis2_man..pdf> via <url:http://products.introgen.com/ivgn/product/V36520.
Nakagawa, et al. Perturbation of insulin-receptor interactions by intramolecular hormone cross-linking. Analysis of relative movement among residues A1,B1, and B29. J Biol Chem. Jan. 5, 1989;264(1):272-9.
Chang, et al. Human insulin production from a novel mini-proinsulin which has high receptor-binding activity. Biochem J. Feb 1, 1998; 329 (Pt 3):631-5.
Bhatla, et al. Use of oil bodies and oleosins in recombinant protein production and other biotechnological applications. Biotechnol Adv. May-Jun 2010;28(3):293-300. doi: 10.1016/j .biotechadv.2010.01.001. Epub Jan. 11, 2010.
Fonda, et al. Attachment of histidine tags to recombinant tumor necrosis factor-alpha drastically changes its properties. ScientificWorldJournal. May 15, 2002;2:1312-25.
International search report and written opinion dated Jan. 12, 2015 for PCT/US2014/034411.

* cited by examiner

*Primary Examiner* — Julie Ha
*Assistant Examiner* — Kristina M Hellman
(74) *Attorney, Agent, or Firm* — Wilson Sonsini Goodrich & Rosati

(57) ABSTRACT

The subject matter of this invention is directed towards chemically and thermodynamically stable single-chain insulin (SCI) analogues that are resistant to deamidation and fibrillation. The invention further discloses improved methods for the recombinant expression, purification and refolding of SCI.

20 Claims, 2 Drawing Sheets

1A.

1B.

1C.

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 1

Tyr Pro Gly Asp Xaa
1               5

<210> SEQ ID NO 2
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      affinity tag peptide
<220> FEATURE:
<221> NAME/KEY: misc_feature
<222> LOCATION: (1)..(10)
<223> OTHER INFORMATION: This sequence may encompass 5-10 residues

<400> SEQUENCE: 2

Lys Lys Lys Lys Lys Lys Lys Lys Lys Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      affinity tag peptide
<220> FEATURE:
<221> NAME/KEY: misc_feature
<222> LOCATION: (1)..(10)
<223> OTHER INFORMATION: This sequence may encompass 5-10 residues

<400> SEQUENCE: 3

His His His His His His His His His His
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      affinity tag peptide
<220> FEATURE:
<221> NAME/KEY: misc_feature
<222> LOCATION: (1)..(10)
<223> OTHER INFORMATION: This sequence may encompass 5-10 residues

<400> SEQUENCE: 4

Glu Glu Glu Glu Glu Glu Glu Glu Glu Glu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      affinity tag peptide
<220> FEATURE:
<221> NAME/KEY: misc_feature
<222> LOCATION: (1)..(10)
<223> OTHER INFORMATION: This sequence may encompass 5-10 residues

<400> SEQUENCE: 5

Arg Arg Arg Arg Arg Arg Arg Arg Arg Arg
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      affinity tag peptide

<400> SEQUENCE: 6

His His His His His His
1               5
```

```
<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      affinity tag peptide

<400> SEQUENCE: 7

Lys Lys Lys Lys Lys Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      affinity tag peptide

<400> SEQUENCE: 8

Glu Glu Glu Glu Glu Glu
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      affinity tag peptide

<400> SEQUENCE: 9

Arg Arg Arg Arg Arg Arg
1               5

<210> SEQ ID NO 10
<211> LENGTH: 21
<212> TYPE: PRT
<213> ORGANISM: Homo sapiens

<400> SEQUENCE: 10

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 11
<211> LENGTH: 30
<212> TYPE: PRT
<213> ORGANISM: Homo sapiens

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

US 9,006,176 B2

CHEMICALLY AND THERMODYNAMICALLY STABLE INSULIN ANALOGUES AND IMPROVED METHODS FOR THEIR PRODUCTION

This application claims priority under 35 U.S.C. 119(e) to U.S. Provisional Application 61/548,721, filed Oct. 18, 2011, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Feb. 21, 2013, is named 39538-706-201-Seqlist.txt and is 4 Kilobytes in size.

TECHNICAL FIELD

The present invention relates to the recombinant vector construct and recombinant production of a single chain insulin (SCI) analog that is chemically and thermodynamically stable. The present invention also relates to a method of introducing said SCI into at least one mammalian tissue for use in treating diabetes in the mammalian host.

BACKGROUND

Efforts to improve the standard of insulin therapy have been driven largely by consideration of the needs of the affluent, western diabetic patient. Substantial improvements have been realized in optimized glucose control, with the introduction of prandial and basal insulin analogs as well as basal/bolus insulin mixtures. Increased convenience and compliance has been achieved through the introduction of insulin pens and electronically controlled pumps. In addition, recent attempts have been made to offer alternatives to subcutaneous injection through the development of pulmonary delivery systems.

While noteworthy, these advances have left the more fundamental and urgent needs of the developing world patients largely unmet. As epidemiological trends suggest, it is the developing world diabetic population that is experiencing the most rapid growth. Chief among the problems facing this population is the limited stability of the conventional insulin preparations. Package inserts typically recommend storing unopened vials at 2° C. to 8° C. and discarding vials 28 days after opening. While this limitation rarely poses problems for western populations, it does impose hardships for users in developing countries where access to refrigeration is limited and temperatures may exceed 25° C. for extended periods of time. The needs of these patients need to be addressed with meaningful advances certain to have an impact from both an economic and humanitarian standpoint. Additionally, a more stable insulin with a reduced tendency toward fibrillation would be well suited for use in pumps and similar infusion devices where clogging problems can be a hazard.

SUMMARY OF THE INVENTION

One object of the invention is a composition of matter that comprises a single chain insulin (SCI) that has one or more of the following properties compared to native insulin: resists fibrillation better than native insulin, shows enhanced resistance to deamidation at B3 and/or A21, exhibits at least 50% of the in vitro potency of native insulin, maintains an insulin receptor vs. IGF-1 receptor selectivity similar to native insulin, and shows superior stability at 25° C. for up to 3 months. In various embodiments, the SCI has two, three, four, or all five of the listed properties.

A further object of the invention includes recombinant methods for efficiently producing single chain insulin (SCI).

In various embodiments, a single-chain insulin analog compound is provided:

Stable B chain-C'-Stable A chain      Formula (I)

wherein Stable B and Stable A chains are modified human insulin chains, respectively, that are resistant to chemical degradation, and C' is a joining peptide of from 5 to 9 amino acids. In various embodiments, C' is designed to provide enhanced thermal stability and fibrillation resistance. In various embodiments, the analog of Formula (I) has the properties of higher insulin receptor binding activity than proinsulin and low IGF-1 binding affinity.

Another object of the invention is to provide a polynucleotide encoding the single-chain insulin analog described above. Another embodiment of the invention includes a recombinant vector comprising the polynucleotide that encodes the single chain insulin analog described above. The vector may be a plasmid with an inducible promoter. More preferably, the promoter may be regulated by glucose. The invention is also directed to a cell line transformed with the above-described vector.

The present invention also encompasses a method for treating a patient suffering from diabetes comprising administering the single chain insulin analog compound as described to a patient in need thereof. Preferably, the diabetes is type I diabetes.

These and other objects of the invention will be more fully understood from the following description of the invention, the referenced drawings, and the claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A discloses SEQ ID No: 10 and SEQ ID No: 11, respectively, in order of appearance.

DETAILED DESCRIPTION

Figure 1:
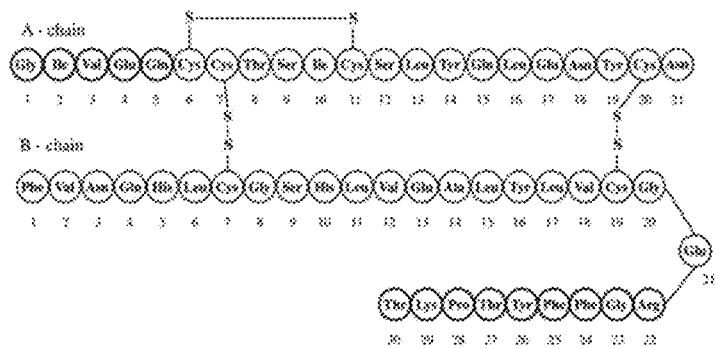
FIG. 1A: Schematic of two chain human insulin.
FIG. 1B: Three dimensional rendering of two chain insulin.
FIG. 1C: Three dimensional rendering of single chain insulin (SCI) where the optimized beta-turn sequence is represented connecting subunits A and B.
Figure 1:
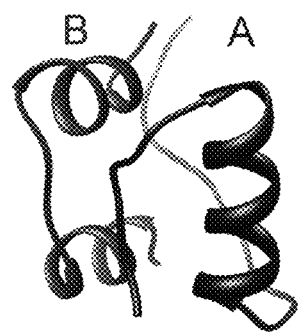
Figure 1:
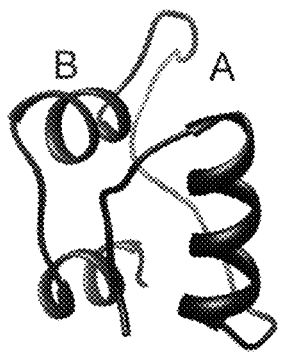
Figure 2:
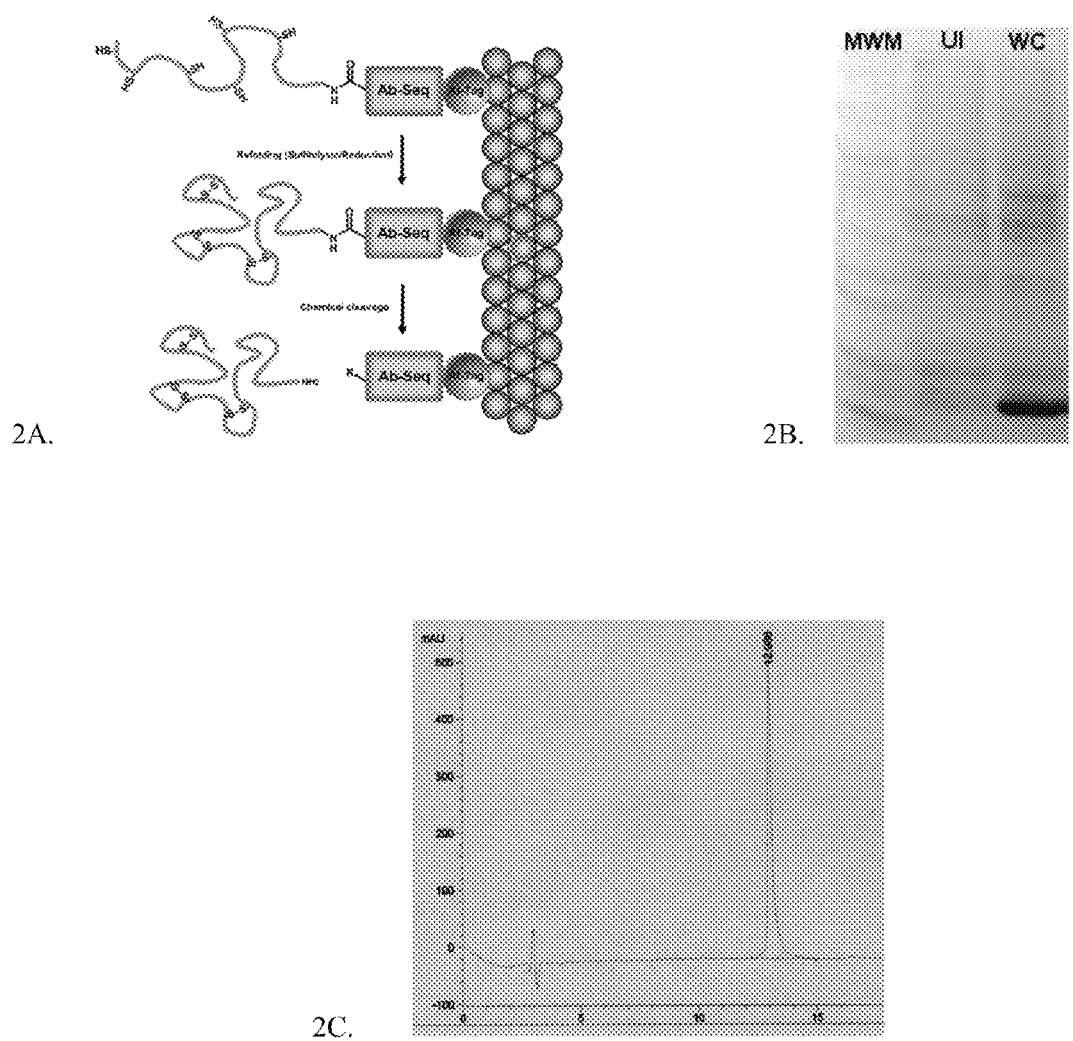
FIG. 2A: Diagram of purification process. In the diagram, a fusion peptide including a chemical cleavage tag and an affinity tag are bound to a solid support under conditions with free thiol groups. The fusion peptide is exposed to refolding conditions (sulfolysis/reduction). After formation of disulfide bonds, a chemical cleavage step is performed, thus liberating the folded protein with an amino terminus.
FIG. 2B: SDS-PAGE showing high level expression of the fusion peptide (expressed SCI construct and affinity tag). MWM is molecular weight marker, UI is uninduced cells and WC is induced cells. The high level of fusion protein expression accounts for more than 40% of the total protein.
FIG. 2C: Reverse phase HPLC trace of purified refolded SCI purified as described within the present disclosure.

Disclosed herein are methods for producing fusion peptides that can be purified and cleaved into desired peptides, and the peptides produced according to the methods. In various embodiments, the method includes induction, inclusion body isolation, affinity column purification, and chemical cleavage. In various embodiments, methods and compositions described herein utilize an expression vector to make the peptides described herein. In some aspects, by combining molecular expression technologies that employ genetically-malleable microorganisms such as E. coli cells to synthesize a peptide of interest with post-expression isolation and modification, one can synthesize a desired peptide rapidly and efficiently. In various embodiments, methods and compositions described herein produce fusion peptides that can be purified using affinity separation and cleaved with a chemical reagent to release a target peptide, including a single chain insulin target peptide.

In various embodiments, methods and compositions described herein are directed to a vector that encodes an inclusion body targeting sequence, an affinity tag to facilitate purification, and a specific amino acid sequence that facilitates selective chemical cleavage. Variously, the inclusion body targeting amino acid sequence comprises from about 1 to about 125 amino acids of a ketosteroid isomerase protein or residues of oleosin, preferably residues up to residues 1-52, with or without amino acid substitutions. Such amino acid substitutions may improve chromatographic purification. The affinity tag sequence may comprise a poly-histidine, a poly-lysine, poly-aspartic acid, or poly-glutamic acid. In one embodiment, the vector further comprises an expression promoter located on the 5' end of the affinity tag sequence. In one embodiment, methods and compositions described herein are directed to a vector that codes for a specific sequence that facilitates selective chemical cleavage to yield a peptide of interest following purification. Such chemically cleavable amino acid sequences include Trp, His-Met, or Pro-Met.

In one embodiment, methods and compositions described herein utilize a peptide expression vector, comprising: a) a first nucleotide sequence encoding an affinity tag amino acid sequence; b) a second nucleotide sequence encoding an inclusion body targeting amino acid sequence; c) a third nucleotide sequence encoding a chemically cleavable amino acid sequence; and d) a promoter in operable combination with the first, second, and third nucleotide sequences.

In one embodiment, methods and compositions described herein produce a single chain insulin (SCI) peptide of commercial or therapeutic interest comprising the steps of: a) cleaving a vector with a restriction endonuclease to produce a cleaved vector; b) ligating the cleavage site to one or more nucleic acids, wherein the nucleic acids encode a desired peptide having at least a base overhang at each end configured and arranged for ligation with the cleaved vector to produce a second vector suitable for expression of a fusion peptide; c) transforming the second vector into suitable host cell; d) incubating the host cell under conditions suitable for expression of fusion peptide; e) isolation of inclusion bodies from the host cell; f) solubilization and extraction of the fusion peptide from the inclusion bodies; g) binding of the fusion peptide to a suitable affinity material; h) washing of bound fusion peptide to remove impurities; and i) cleaving the fusion peptide to release the said target SCI peptide.

SCI produced by methods and compositions described herein may have significantly lower costs and/or other advantageous features. These potentially cheaper costs may lie not only in less expensive raw materials required for production, but also may lie in less chemical waste which is generated compared to the traditional process of solid phase peptide synthesis, or in more efficient processing to achieve a certain purity, thus lowering the cost of the material. Furthermore, the exclusion of a waste stream may be particularly beneficial to the environment. In various embodiments, processes according to methods and compositions described herein provide a high yield of SCI with high purity. In various embodiments, SCI produced according to methods and compositions described herein may be R&D grade or clinical grade.

Definitions

Unless defined otherwise, all technical and scientific terms used herein have the same meaning as commonly understood by a person of ordinary skill in the art.

As used herein, the term "peptide" is intended to mean any polymer comprising amino acids linked by peptide bonds. The term "peptide" is intended to include polymers that are assembled using a ribosome as well as polymers that are assembled by enzymes (i.e., non-ribosomal peptides) and polymers that are assembled synthetically. In various embodiments, the term "peptide" may be considered synonymous with "protein," or "polypeptide." In various embodiments, the term "peptide" may be limited to a polymer of greater than 50 amino acids, or alternatively, 50 or fewer amino acids. In various embodiments, the term "peptide" is intended to include only amino acids as monomeric units for the polymer, while in various embodiments, the term "peptide" includes additional components and/or modifications to the amino acid backbone. For example, in various embodiments, the term "peptide" may be applied to a core polymer of amino acids as well as derivatives of the core polymer, such as core polymers with pendant polyethylene glycol groups or core polymers with amide groups at the amino or carboxy terminus of the amino acid chain.

As used herein, "consisting essentially of" may exclude those features not listed herein that would otherwise alter the operation of methods and compositions described herein. However, the use of the phrase "consisting essentially of" does not exclude features that do not alter the operation of the required components.

As used herein, the term "patient" includes members of the animal kingdom including but not limited to human beings. As used herein, the term "mammalian host" includes members of the animal kingdom including but not limited to human beings. The term "mammal" is known in the art, and exemplary mammals include human, primate, bovine, porcine, canine, feline, and rodent (e.g., mice and rats).

As used herein, the term "diabetes" is a hormonal disorder, the term "Type I diabetes" means insulin-dependent diabetes mellitus (IDDM), and the term "Type II diabetes" means non insulin-dependent diabetes mellitus (NIDDM).

As used herein, a "promoter" can be any sequence of DNA that is active, and controls transcription in a eukaryotic cell.

Insulin is composed of two peptide chains referred to as the A chain and the B chain. The A and B chains are linked together by two disulfide bonds, and an additional disulfide is formed within the A chain. In most species, the A chain consists of 21 amino acids and the B chain of 30 amino acids. Although the amino acid sequence of insulin varies among species, certain segments of the molecule are highly conserved, including the positions of the three disulfide bonds, both ends of the A chain, and the C-terminal residues of the B chain. These similarities in the amino acid sequence of insulin lead to a three dimensional conformation of insulin (FIG. 1) that is very similar among species, and insulin from one animal is very likely biologically active in other species. Indeed, pig insulin has been widely used to treat human patients.

Regulatory agencies specify requirements for not only insulin potency but also set a specific limit on the level of impurities present in the commercial formulation. For example, the US Pharmacopeia specifies that human insulin is to have a "potency of not less than 95%, nor more than 105%" of the stated potency. In addition, depending on the type of insulin it specifies a limit of no more than 1.0-1.5% for HMWP impurity content and a "related impurities" content of not more that 2% for 21-desamidoinsulin and 2% total for all other impurities.

Insulin molecules have a tendency to form dimers in solution due to hydrogen-bonding between the C-termini of B chains. Additionally, in the presence of zinc ions, insulin dimers associate into hexamers. These interactions have important clinical ramifications. Monomers and dimers readily diffuse into blood, whereas hexamers diffuse very poorly. Hence, absorption of insulin preparations containing a high proportion of hexamers is delayed and slow.

An important characteristic of formulated insulin which significantly limits both storage and in use stability is a propensity to undergo fibrillation, an irreversible non-covalent polymerization process which causes the insulin molecules to aggregate and form insoluble linear fibrils. The process is most favored under acidic pH and elevated temperature conditions, and is exacerbated by agitation and by the presence of excess zinc ions. The consequences of increased insulin fibril content include a gradual attenuation of the pharmacological potency of the insulin preparation as well as the possibility of increased immunogenicity. Mechanistically, this complex phenomenon is thought to be initiated through displacement or "unfolding" of the B-chain C-terminus and the resulting exposure of the non-polar residues IleA2, ValA3, LeuB11 and LeuB15 which then form a hydrophobic interface facilitating the fibrillation event.

The tendency towards fibrillation can be effectively minimized in cases where C-terminal residues of the B-chain are conformationally restricted by tethering to the N-terminus of the A-chain thereby forming a continuous single chain insulin (SCI). For example, proinsulin is significantly less prone to fibrillation than insulin and cleavage of its C-peptide readily restores the fibrillation tendency. Other SCI peptides with shorter C-peptides have been shown to resist fibrillation. Conversely, C-terminally truncated analogs such des(B26-30) insulin are known to fibrillate even more rapidly than native insulin, supporting the view that the B-chain C-terminus plays a critical role in the fibrillation process.

Long term chemical stability of insulin is affected by pH and temperature. In addition, there are a number of secondary factors which can influence long-term stability. These include the type of crystal structure, the presence of bacteriostatic agents (phenol, m-cresol), buffering reagents (phosphate, TRIS), isotonicity additives (glucose, glycerol, NaCl), and substances added to protract insulin's time of action profile (protamine sulfate and Zn++).

With regard to chemical degradation patterns of human insulin, while any of the six amide containing side chains in insulin (GlnA5, GlnA15, AsnA18, AsnA21, AsnB3, GlnB5) can undergo deamidation, in the context of commercial formulations only the asparagines at A21 and B3 are of specific concern. Of the two, AsnA21 is the more labile site with up to 20-30% deamidation noted after one year in acidic formulations. Mechanistically, the AsnA21 degradation proceeds via an aspartimide intermediate to give either the aspartic acid derivative, or through reaction with another insulin molecule, a covalent insulin dimer (CID) or higher order molecular weight transformation (HMWT) product. AsnB3 hydrolytic decomposition occurs under neutral conditions and results in formation of AspB3 and isoAspB3 in roughly equal proportions. In certain crystalline zinc formulations, the A-chain also undergoes backbone cleavage between ThrA8 and SerA9.

Single chain insulin (SCI) according to the invention encompasses a group of structurally-related proteins wherein the A and B chains are covalently linked by a polypeptide linker. SCI has the property of greater insulin receptor binding activity and/or glucose uptake activity compared to proinsulin, and lesser insulin receptor binding activity and glucose uptake activity compared to insulin. Modification of the linker provides substantial thermodynamic stability in various embodiments.

In SCI according to the invention, a polypeptide linker connects the C-terminus of the B chain to the N-terminus of the A chain. The linker may be of any length so long as the linker provides the structural conformation necessary for SCI to have a glucose uptake and insulin receptor binding effect. Preferably, the linker is about 5-9 amino acids long. Most preferably it is 5 amino acids long. The most preferred sequence for the linker is Y-P-G-D-X (SEQ ID NO:1) wherein X is any amino acid. However, it should be understood that many variations of this sequence are possible such as in the length (both addition and deletion) and substitutions of amino acids without substantially compromising the effectiveness of the produced SCI in glucose uptake and insulin receptor binding activities. For example, several different amino acid residues may be added or taken off at either end without substantially decreasing the activity of the produced SCI. In addition, the amino acid Gly may be replaced with any amino acid residue. It is also to be understood that the insulin A and B chains are modified in various embodiments to enhance chemical stability.

While not wishing to be bound by theory, it is believed that SCI produced according to methods and compositions described herein will have differing levels of residual components from known peptide processes of production. For example, in comparison with peptides of the same sequence produced according to conventional recombinant processes, peptides produced according to methods and compositions described herein may be expected to have fewer residual cellular contaminants upon initial purification. Alternatively, in comparison with peptides of the same sequence produced by conventional synthetic processes, peptides produced according to methods and compositions described herein may be expected to have fewer residual chemical contaminants upon initial purification.

In one embodiment, a dosage form comprising one or more SCI according to the invention may be used for clinical purpose. A clinical purpose includes, but is not limited to, diagnosis, prognosis, therapy, clinical trial, and clinical research. In one embodiment, an SCI is used for studying pharmacokinetics/pharmacodynamics. In one embodiment, a dosage form may be formulated for a particular delivery route. A delivery route includes, but is not limited to, oral, nasal, rectal, intravascular, intraperitoneal, subcutaneous, ocular, dermal and the like. A dosage form may be packaged as tablet, gel, aerosol, fluid, particulate, capsule, powder, film, or a coating. A dosage form may also be delivered via a stent or other invasive device such as an implant. In another embodiment, SCI is lyophilized. In another embodiment, SCI is in solution. In another embodiment, SCI is provided as a concentrate accompanied with an appropriate dilution solution and instruction. In another embodiment, SCI is in powdered form. In another embodiment, SCI is provided as gel or in other viscous material such as polyethylene glycol. In another embodiment, SCI is provided in a micelle such as a liposome.

Vectors

A "promoter" can be any sequence of DNA that is active, and controls transcription in a eukaryotic cell. Preferably, the promoter is active in mammalian cells. The promoter may be constitutively expressed or inducible. Preferably, the promoter is inducible. Preferably, the promoter is inducible by an external stimulus. More preferably, the promoter is inducible by hormones or metabolites. Still more preferably, the promoter is regulatable by glucose. Even more preferably, the promoter is a pyruvate kinase gene promoter. In various embodiments, the promoter is a hepatocyte-specific L-type pyruvate kinase gene promoter.

Enhancer elements, which control transcription, can be inserted into a DNA vector construct for the production of SCI, and used to enhance the expression of the target of interest.

Inclusion-body Directing Peptides

Inclusion bodies are composed of insoluble and denatured forms of a peptide and are about 0.5-1.3 μm in diameter. These dense and porous aggregates help to simplify recombinant protein production since they have a high homogeneity of the expressed protein or peptide, result in lower degradation of the expressed protein or peptide because of a higher resistance to proteolytic attack by cellular proteases, and are easy to isolate from the rest of the cell due to differences in their density and size relative to the other cellular components. In various embodiments, the presence of inclusion bodies permits production of increased concentrations of the expressed protein or peptide due to reduced toxicity by the protein or peptide upon segregation into an inclusion body. Once isolated, the inclusion bodies may be solubilized to allow for further manipulation and/or purification.

An inclusion-body directing peptide is an amino acid sequence that helps to direct a newly translated protein or peptide into insoluble aggregates within the host cell. Prior to final isolation, in various embodiments, the target SCI peptide is produced as a fusion peptide where the fusion peptide includes as part of its sequence of amino acids an inclusion-body directing peptide. Methods and compositions described herein are applicable to a wide range of inclusion-body directing peptides as components of the expressed fusion protein or peptide.

In various embodiments, the inclusion-body directing peptide is a keto-steroid isomerase (KSI) sequence, a functional fragment thereof, or a functional homolog thereof. In various embodiments, the inclusion-body directing peptide is a BRCA-2 sequence, a functional fragment thereof, or a functional homolog thereof.

Affinity Tag Peptides

According to methods and compositions described herein, a wide variety of affinity tags may be used. Affinity tags useful according to methods and compositions described herein may be specific for cations, anions, metals, or any other material suitable for an affinity column. In one embodiment, any peptide not possessing an affinity tag will elute through the affinity column leaving the desired fusion peptide bound to the affinity column via the affinity tag.

Specific affinity tags according to methods and compositions described herein may include poly-lysine, poly-histidine, poly-glutamic acid, or poly-arginine peptides. For example, the affinity tags may be 5-10 lysines (SEQ ID NO: 2), 5-10 histidines (SEQ ID NO: 3), 5-10 glutamic acids (SEQ ID NO: 4), or 5-10 arginines (SEQ ID NO: 5). In various embodiments, the affinity tag is a hexa-histidine sequence (SEQ ID NO: 6), hexa-lysine sequence (SEQ ID NO: 7), hexa-glutamic acid sequence (SEQ ID NO: 8), or hexa-arginine sequence (SEQ ID NO: 9). Alternatively, the HAT-tag (Clontech®) may be used. In various embodiments, the affinity tag is a His-Trp Ni-affinity tag. Other tags known in the art may also be used. Examples of tags include, but are not limited to, Isopeptag, BCCP-tag, Myc-tag, Calmodulin-tag, FLAG-tag, HA-tag, MBP-tag, Nus-tag, GST-tag, GFP-tag, Thioredoxin-tag, S-tag, Softag, Streptavidin-tag, V5-tag, CBP-tag, and SBP-tag.

Without wishing to be bound by theory, it is believed that the histidine residues of a poly-histidine tag bind with high affinity to Ni-NTA or TALON resins. Both of these resins contain a divalent cation (Ni-NTA resins contain $Mg^{2+}$; TALON resins contain $Co^{2+}$) that forms a high affinity coordination with the His tag.

In various embodiments, the affinity tag has a pI (isoelectric point) that is at least one pH unit separate from the pI of the target SCI peptide. Such difference may be either above or below the pI of the target peptide. For example, in various embodiments, the affinity tag has a pI that is at least one pH unit lower, at least two pH units lower, at least three pH units lower, at least four pH units lower, at least five pH units lower, at least six pH units lower, or at least seven pH units lower. Alternatively, the affinity tag has a pI that is at least one pH unit higher, at least two pH units higher, at least three pH units higher, at least four pH units higher, at least five pH units higher, at least six pH units higher, or at least seven pH units higher.

In various embodiments, the affinity tag is contained within the native sequence of the inclusion body directing peptide. Alternatively, the inclusion body directing peptide is modified to include an affinity tag. For example, in one embodiment, the affinity tag is a KSI, oleosin N-terminus, or BRCA2 sequence modified to include extra histidines, extra lysines, extra arginines, or extra glutamic acids.

In various embodiments, epitopes may be used such as FLAG (Eastman Kodak) or myc (Invitrogen) in conjunction with their antibody pairs.

Removal of Target SCI Peptide from Affinity Column via Cleavage

Described herein are numerous methods for cleavage of the fusion peptides containing SCI on the affinity column. In general, the cleavage step occurs by introduction of a cleavage agent which interacts with the cleavage tag of the fusion peptide resulting in cleavage of the fusion peptide and release of the target SCI peptide. Following cleavage, the affinity column may be flushed to elute the SCI target peptide while the portion of the fusion peptide containing the affinity tag remains bound to the affinity column. Following elution of the target peptide, the eluting solution may be condensed to a desired concentration. The target SCI peptide may be further processed and/or packaged for distribution or sale.

Control of the cleavage reaction may occur through chemical selectivity. For example, the cleavage tag may include a unique chemical moiety which is absent from the remainder of the fusion peptide such that the cleavage agent selectively interacts with the unique chemical moiety of the cleavage tag.

In various embodiments, control of the cleavage reaction occurs through a unique local environment. For example, the cleavage tag may include a chemical moiety that is present elsewhere in the fusion peptide, but the local environment differs resulting in a selective cleavage reaction at the cleavage tag. For example, in various embodiments, the cleavage tag includes a tryptophan and a charged amino acid side chain within five amino acids of the tryptophan. In various embodiments, the charged amino acid is on the amino terminus of the tryptophan amino acid.

In various embodiments, control of the cleavage reaction may occur through secondary or tertiary structure of the fusion peptide containing SCI. For example, in various embodiments, where identical moieties are present in the cleavage tag and elsewhere in the fusion peptide, the other portions of the fusion peptide may fold in secondary or tertiary structure such as alpha-helices, beta-sheets, and the like, or through disulfide linkages to physically protect the susceptible moiety, resulting in selective cleavage at the cleavage tag.

In various embodiments, minor or even major differences in selectivity of the cleavage reaction for the cleavage tag over other locations in the fusion peptide may be amplified by controlling the kinetics of the cleavage reaction. For example, in various embodiments, the concentration of cleavage agent is controlled by adjusting the flow rate of eluting solvent containing cleavage agent. In various embodiments, the concentration of cleavage agent is maintained at a low level to amplify differences in selectivity. In various embodiments, the reservoir for receiving the eluting solvent contains a quenching agent to stop further cleavage of target peptide that has been released from the column.

Moreover, various methods for removal of peptides from affinity columns may be excluded. For example, in some embodiments, the steps of removal may specifically exclude the step of washing an affinity column with a solution of a compound with competing affinity in the absence of a cleavage reaction. In one embodiment, the step of washing an affinity column with a solution of imidazole as a displacing agent to assist in removing a fusion peptide from an affinity column is specifically excluded. The concentration of imidazole may vary. For example, the concentration of imidazole to wash the column may include about 1-10 mM, 5-20 mM, 10-50 mM, 30-70 mM, 50-100 mM, 80-200 mM, 100-300 mM, 150-500 mM. Imidazole may be applied as a fixed concentration or as a gradient between two fixed concentration representing the lower and the upper limits. For example, a gradient of imidazole may be used to wash the column, starting from 1 mM and ending with 500 mM over a period of time.

In various embodiments, the cleavage agent is selected from the group consisting of NBS, NCS, cyanogen bromide, Pd(H2O)4, 2-ortho iodobenzoic acid, DMSO/sulfuric acid, or a proteolytic enzyme. Various methods and cleavage agents are described in detail herein.

A. NBS Cleavage

In one embodiment, the cleavage reaction according to methods and compositions described herein involves the use of a mild brominating agent N¬bromosuccinimde (NBS) to selectively cleave a tryptophanyl peptide bond at the amino terminus of the SCI peptide. Without wishing to be bound by theory, it is believed that in aqueous and acidic conditions, NBS oxidizes the exposed indole ring of the tryptophan side chain, thus initiating a chemical transformation that results in cleavage of the peptide bond at this site. Accordingly, the active bromide ion halogenates the indole ring of the tryptophan residue followed by a spontaneous dehalogenation through a series of hydrolysis reactions. These reactions lead to the formation of an oxindole derivative which promotes the cleavage reaction.

B. NCS Cleavage

In one embodiment, the cleavage reaction according to methods and compositions described herein involves the use of a mild oxidizing agent N¬chlorosuccinimde (NCS) to selectively cleave a tryptophanyl peptide bond at the amino terminus of the target peptide. Without wishing to be bound by theory, it is believed that in aqueous and acidic conditions, NCS oxidizes the exposed indole ring of the tryptophan side chain, thus initiating a chemical transformation that results in cleavage of the peptide bond at this site.

Peptide Marketing

Described herein are methods directed to marketing the target SCI peptides. In one embodiment, the commercial market for a target SCI peptide is evaluated. Evaluative methods may include, but are not limited to, producing a target SCI peptide as described herein, making sample amounts of the target peptide available for no cost or for minimal cost, and measuring the number of requests for the target peptide over a period of time. Advantages of making a target peptide available in this manner may include an improved calculation of the future supplies needed and/or future demand by paying customers. Alternatively, providing a target peptide at no cost or minimal cost initially may induce interest in the target peptide and the discovery of favorable characteristics for the peptide that spur future sales. Minimal cost may include a price that is approximately the cost of production with essentially no profit involved. In various embodiments, the minimal cost may be about 10%, about 20%, about 30%, about 40%, about 50%, about 60%, or about 70% of the price of a competitor's product.

In one aspect, SCI described herein is provided as a kit. In another embodiment, a kit comprises amino acids, a vector, a host organism, and an instruction manual. In another embodiment, a kit comprises amino acids, a vector, a host organism, a Ni+ column, imidazole, and an instruction manual. In another embodiment, a kit comprises an instruction manual describing methods and compositions disclosed herein. In another embodiment, a kit comprises SCI and a medical device for delivery of the SCI to a patient in need thereof.

EXAMPLES

Example 1

Cloning and Expression of Single Chain Insulin (SCI) DNA in *E. coli*

Cells are induced to initiate the synthesis of KSI-SCI with 1 mM IPTG (Invitrogen) and 0.2% L-arabinose (Calbiotech) as follows. Plated cells are incubated overnight at 37° C. and then one colony from this plate is grown up overnight in a starter culture of 8 mL of Luria broth+ampicillin. The following morning, the starter culture is inoculated into 1 L of Luria broth+ampicillin and grown to an optical density (OD) of 0.5. At this point, the cells are induced with 1 mM IPTG (Invitrogen) and 0.2% L-arabinose (Calbiotech) to initiate the synthesis of KSI-SCI.

To optimize the amount of KSI-SCI production in the bacteria, samples of the 1 L inoculation are taken prior to inducing the bacteria, and then 2, 4, 6, and 16 hours (overnight growth) after induction. An acrylamide gel is used to analyze the samples.

Eight hours after induction, the cells are re-induced with the same concentrations of IPTG and L-arabinose as well as 100 mg of ampicillin as to prevent the growth of any new strains of E. coli.

Example 1A

The construct is re-designed to place a His-tag upstream from the KSI sequence rather than downstream.

Example 2

Following induction of KSI-SCI production in E. coli, lysis buffer containing 25 mM Tris pH 8.0, 50 mM NaCl, 10% glycerol, and the protease inhibitor 1000×PMSF is added before lysis. Insoluble inclusion bodies are collected using washing and centrifugation. Three different wash buffers are used containing varying concentrations of Tris pH 8.0, NaCl, and Triton X100. Once washed clean of the remaining cellular components, the insoluble inclusion bodies are solubilized in a buffer containing 25 mM Tris pH 8.0, 50 mM, NaCl, 0.1 mM PMSF, and 8M urea. The 8M urea serves as a chaotropic agent necessary in solubilizing protein.

An acrylamide gel is run on both uninduced and induced bacteria, the cell lysate produced from high output sonication, and the supernatant from each washing step during the inclusion body preparation. The gel is stained with Coomassie Blue reagent. The appearance of a band in the induced sample provides evidence for inclusion body synthesis resulting from induction. Exemplary data shows the stages of inclusion body preparation by gel electrophoresis of cells lysed with high-power sonication and washed with a series of buffers containing different concentrations of Tris, NaCl, PMSF, Triton-X100, and urea. The disappearance of the band during successive steps and reappearance of the band upon solubilizing the inclusion bodies indicates that inclusion bodies are properly prepared. Accordingly, a lane containing cell lysate is almost entirely blue because as the cells are ruptured, relatively large quantities of various proteins are extracted. As the lysate is washed repeatedly of impurities, the lanes become clearer.

Example 3

Ni-NTA Affinity Chromatography resin purchased from Invitrogen is equilibrated with the same solubilization buffer as in the inclusion body preparation. Next, the resin is charged with the solubilized inclusion bodies and the flow through is collected. The column is then washed with five column volumes of 50% ethanol to remove urea and flow through.

Example 4

After washing with ethanol to remove urea, 3×NBS is loaded and the column is placed on a rocker for 30 minutes. The reaction is quenched with excess N-acetylmethionine and the flow through is collected. The column is then washed with 300 mM imidazole to discharge any remaining protein and the flow through is collected.

Example 4a

Exemplary data for gel electrophoresis following Ni-NTA affinity chromatography is as follows. Inclusion bodies are loaded onto an equilibrated Ni-NTA column and washed with the same buffer, collecting the flow-through. The column is then washed with 50% ethanol as to equilibrate it with cleavage solution buffer. On-column cleavage is performed with 3×NBS for 30 minutes at room temperature and the flow through is collected. The column is washed with 300 mM imidazole to wash off all remaining fusion protein and the flow-through is collected.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A single chain insulin (SCI) compound of formula a(I):

B chain -C'-A chain     (Formula (I))

having the properties of higher affinity for the insulin receptor and lower affinity for the IGF-1 receptor as compared to those of native proinsulin with chemical and thermodynamic degradation profiles such that the SCI can be formulated and stored for extended periods of time without refrigeration;

wherein B chain and A chain are modified human insulin chains; and wherein C' covalently links the C-terminus of the B chain to the N-terminus of the A chain, and is a peptide of 5 amino acids comprising the following sequence: Y-P-G-D-X (SEQ ID NO: 1); wherein X is any amino acid;

wherein the B chain is modified from a native human insulin B chain (SEQ ID NO:11), and A chain is modified from a native human insulin A chain (SEQ ID NO:10), wherein the modifications comprise one or more mutations at (1) Gln5, Gln15, Asn18, or Asn21 of SEQ ID NO:10, or (2) Asn3 or Gln5 of SEQ ID NO:11; resulting in enhanced resistance to deamidation.

2. The SCI according to claim 1, wherein the modifications comprise mutations at AsnA21 and AsnB3.

3. A polynucleotide comprising a nucleic acid sequence that encodes the single chain insulin compound according to claim 1.

4. A recombinant vector comprising the polynucleotide according to claim 3.

5. The recombinant vector according to claim 4, wherein said vector is a plasmid.

6. The recombinant vector according to claim 4, comprising an inducible promoter.

7. The recombinant vector according to claim 6, wherein said inducible promoter is IPTG.

8. The recombinant vector according to claim 4, comprising a fusion tag.

9. The recombinant vector according to claim 8, wherein the fusion tag is derived from oleosin.

10. The recombinant vector accordingly to claim 8, wherein said fusion tag encodes a chemically cleavable sequence.

11. A cell line transformed with the vector according to claim 4.

12. A method for treating diabetes in a patient in need thereof comprising administering a single chain insulin (SCI) compound of formula (I):

B chain -C'-A chain     (Formula (I))

having the properties of higher affinity for the insulin receptor and lower affinity for the IGF-1 receptor as compared to those of native proinsulin with chemical and thermodynamic degradation profiles such that the SCI can be formulated and stored for extended periods of time without refrigeration;
wherein B chain and A chain are modified human insulin chains; and
wherein C' covalently links the C-terminus of the B chain to the N-terminus of the A chain, and is a peptide of 5 amino acids comprising the following sequence: Y-P-G-D-X (SEQ ID NO: 1); wherein X is any amino acid;
wherein the B chain is modified from a native human insulin B chain (SEQ ID NO:11), and A chain is modified from a native human insulin A chain (SEQ ID NO:10), wherein the modifications comprise one or more mutations at (1) Gln5, Gln15, Asn18, or Asn21 of SEQ ID NO:10, or (2) Asn3 or Gln5 of SEQ ID NO:11; resulting in enhanced resistance to deamidation.

13. The method of claim 12, wherein the diabetes is type I diabetes.

14. A method for producing single chain insulin (SCI) comprising introducing a recombinant vector into an expression system, expressing a protein comprising a fusion tag and single chain insulin, cleaving said fusion tag from said single chain insulin, and isolating said single chain insulin, wherein the recombinant vector comprises a polynucleotide comprising a nucleic acid sequence that encodes the SCI of formula (I):

B chain -C'-A chain     (Formula (I))

having the properties of higher affinity for the insulin receptor and lower affinity for the IGF-1 receptor as compared to those of native proinsulin with chemical and thermodynamic degradation profiles such that the SCI can be formulated and stored for extended periods of time without refrigeration;
wherein B chain and A chain are modified human insulin chains; and
wherein C' covalently links the C-terminus of the B chain to the N-terminus of the A chain, and is a peptide of 5 amino acids comprising the following sequence: Y-P-G-D-X (SEQ ID NO: 1); wherein X is any amino acid;
wherein the B chain is modified from a native human insulin B chain (SEQ ID NO:11), and A chain is modified from a native human insulin A chain (SEQ ID NO:10), wherein the modifications comprise one or more mutations at (1) Gln5, Gln15, Asn18, or Asn21 of SEQ ID NO:10, or (2) Asn3 or Gln5 of SEQ ID NO:11; resulting in enhanced resistance to deamidation.

15. A method for obtaining purified single chain insulin (SCI) comprising producing said SCI according to claim 14, further comprising the step of affinity chromatography.

16. A single chain insulin (SCI) compound of formula (I):

B chain -C'-A chain     (Formula I));

having the properties of higher affinity for the insulin receptor and lower affinity for the IGF-1 receptor as compared to those of native proinsulin with chemical and thermodynamic degradation profiles such that the SCI can be formulated and stored for extended periods of time without refrigeration;
wherein the B chain and A chain are native or modified human insulin chains; and
wherein C' covalently links the C-terminus of the B chain to the N-terminus of the A chain, and is a peptide of 5 amino acids comprising the following sequence: Y-P-G-D-X (SEQ ID NO: 1); wherein X is any amino acid.

17. The SCI of claim 16, wherein the B chain is modified from a native human insulin B chain (SEQ ID NO:11).

18. The SCI of claim 17, wherein the modifications comprise one or more mutations at Asn3 or Gln5 of SEQ ID NO:11.

19. The SCI of claim 16, wherein the A chain is modified from a native human insulin A chain (SEQ ID NO:10).

20. The SCI of claim 19, wherein the modifications comprise one or more mutations at Gln5, Gln15, Asn18, or Asn21 of SEQ ID NO:10.

* * * * *